(12) United States Patent
Patel et al.

(10) Patent No.: US 8,328,870 B2
(45) Date of Patent: Dec. 11, 2012

(54) STAND-ALONE INTERBODY FIXATION SYSTEM

(75) Inventors: Nirali Patel, Murrieta, CA (US); Yang Cheng, Foothill Ranch, CA (US); Fred Murrillo, San Diego, CA (US); Thomas Purcell, Del Mar, CA (US); Jens Peter Timm, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 32 days.

(21) Appl. No.: 12/852,033

(22) Filed: Aug. 6, 2010

(65) Prior Publication Data

US 2011/0035007 A1 Feb. 10, 2011

Related U.S. Application Data

(60) Provisional application No. 61/231,967, filed on Aug. 6, 2009.

(51) Int. Cl.
*A61F 2/44* (2006.01)
(52) U.S. Cl. .................................... 623/17.11
(58) Field of Classification Search .... 623/17.11–17.16; 606/246, 248–249
See application file for complete search history.

(56) References Cited

U.S. PATENT DOCUMENTS

| | | | | |
|---|---|---|---|---|
| 5,683,394 A | * | 11/1997 | Rinner | 606/86 R |
| 6,527,803 B1 | * | 3/2003 | Crozet et al. | 623/17.11 |
| 6,670,096 B2 | * | 12/2003 | Kawamura et al. | 430/271.1 |
| 6,770,096 B2 | * | 8/2004 | Bolger et al. | 623/17.16 |
| 7,594,932 B2 | * | 9/2009 | Aferzon et al. | 623/17.16 |
| 2007/0270961 A1 | * | 11/2007 | Ferguson | 623/17.11 |
| 2009/0099601 A1 | * | 4/2009 | Aferzon et al. | 606/246 |
| 2009/0164020 A1 | * | 6/2009 | Janowski et al. | 623/17.16 |
| 2010/0106191 A1 | * | 4/2010 | Yue et al. | 606/249 |
| 2011/0054616 A1 | * | 3/2011 | Kamran et al. | 623/17.12 |

\* cited by examiner

*Primary Examiner* — Alvin Stewart
*Assistant Examiner* — Michelle C Eckman
(74) *Attorney, Agent, or Firm* — Michael J. Loi

(57) ABSTRACT

A stand-alone interbody fixation system having a cage, anterior fixation blade and posterior fixation blade. The cage includes an annular side wall with an open interior and upper and lower surfaces, the cage being configured to fit between end plates of adjacent vertebrae. The anterior fixation blade includes an anterior alignment boss with two opposing outward extending anterior blades with end plate penetrating tips configured to fit within the open interior of the cage. The posterior fixation blade includes a posterior alignment boss with two opposing outward extending posterior blades with end plate penetrating tips configured to fit within the open interior of the cage. The anterior alignment boss and posterior alignment boss being rotatably coupled to each other and with a first opening and a second opening in the annular side wall opposite the first opening. The anterior and posterior fixation blades are counter-rotating blades and the anterior alignment boss and posterior alignment boss are configured to receive or engage a blade activation tool having an anterior engagement portion and a posterior engagement portion configured to rotate the anterior and posterior fixation blades from a stowed position to a deployed condition.

18 Claims, 14 Drawing Sheets

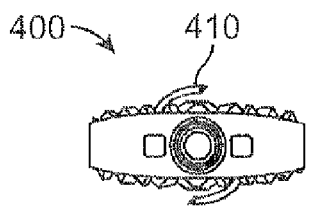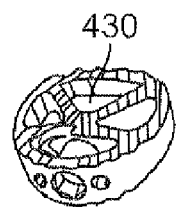
FIG. 12A    FIG. 12B
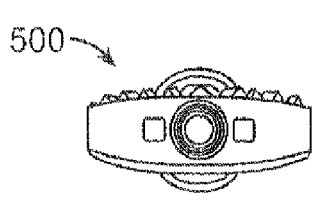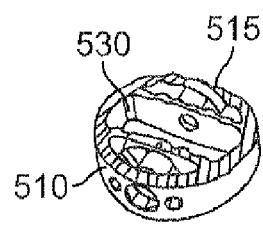
FIG. 13A    FIG. 13B
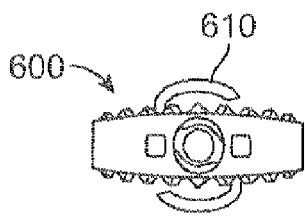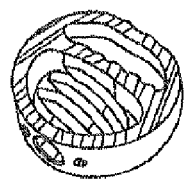
FIG. 14A    FIG. 14B    FIG. 14C
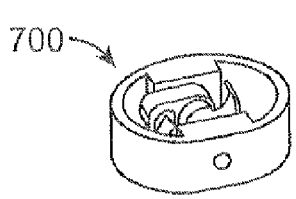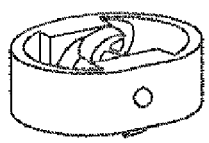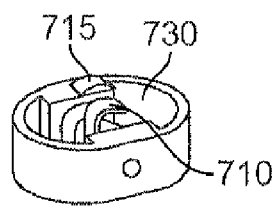
FIG. 15A    FIG. 15B    FIG. 15C
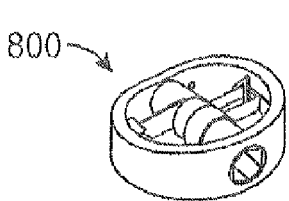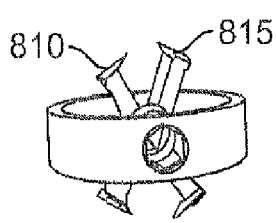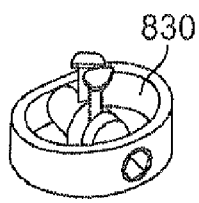
FIG. 16A    FIG. 16B    FIG. 16C

STAND-ALONE INTERBODY FIXATION SYSTEM

CROSS-REFERENCES TO RELATED APPLICATIONS

The present application claims priority from U.S. Provisional Application No. 61/231,967, which was filed on Aug. 6, 2009, and is incorporated herein by reference in its entirety.

BACKGROUND OF THE INVENTION

1. Field of the Invention

The present invention generally relates to the field of spinal orthopedics, and more particularly to methods and systems for securing interbody cages within the intervertebral space.

2. Background

The spine is a flexible column formed of a plurality of bones called vertebra. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies.

The intervertebral fibro-cartilages are also known as intervertebral disks and are made of a fibrous ring filled with pulpy material. The disks function as spinal shock absorbers and also cooperate with synovial joints to facilitate movement and maintain flexibility of the spine. When one or more disks degenerate through accident or disease, nerves passing near the affected area may be compressed and are consequently irritated. The result may be chronic and/or debilitating back pain. Various methods and apparatus have been designed to relieve such back pain, including spinal fusion using a interbody spacer or suitable graft using techniques such as Anterior Lumbar Interbody Fusion (ALIF), Posterior Lumbar Interbody Fusion (PLIF), or Transforaminal Lumbar Interbody Fusion (TLIF) surgical techniques. The implants used in-these techniques, also commonly referred to as vertebral body replacements (VBR) devices, are placed in the interdiscal space between adjacent vertebrae of the spine. Many times an exterior plate is used in conjunction with the VBR to hold the adjacent vertebrae while the fusion occurs.

Ideally, the interbody spacer should stabilize the intervertebral space and allow fusion of the adjacent vertebrae. Moreover, during the time it takes for fusion to occur, the interbody spacer should have sufficient structural integrity to withstand the stress of maintaining the space without substantially degrading or deforming and have sufficient stability to remain securely in place prior to actual bone ingrowth fusion.

One significant challenge to providing fusion stability (prior to actual bone ingrowth fusion) is preventing spinal extension during patient movement. Distraction of the vertebral space containing the fusion graft may cause the interbody spacer to shift or move disrupting bone ingrowth fusion and causing pain. An exterior plate is often used with the interbody spacer to hold the adjacent vertebrae while the fusion occurs.

There remains a need for an interbody spacer capable of holding the adjacent vertebrae steady during fusion without the use of external plates.

SUMMARY OF THE INVENTION

Generally, embodiments of the present invention provide a stand-alone single fixation system having a cage, an anterior fixation blade and a posterior fixation blade. The anterior and posterior blades may be positioned within the cage in a delivery position and rotated from the cage to a deployed position. The stand-alone interbody fixation system is a pre-assembled multi-component design which integrates a fixation feature with an interbody spacer, no additional support is required. The system may be used in spinal fusion surgeries including ALIF, PLIF and TLIF procedures, wherein two or more vertebrae are joined or fused together for the treatment of spinal disorders such as spondylolisthesis, scoliosis, severe disc degeneration, or spinal fractures. The system may also be used in open and minimally invasive surgery (MIS) procedures, and using low profile instrumentation facilitates a less invasive approach through a smaller incision.

In a first aspect, embodiments of the present invention provide a stand-alone interbody fixation system having a cage, anterior fixation blade and posterior fixation blade. The cage includes an annular side wall with an open interior and upper and lower surfaces, the cage being configured to fit between end plates of adjacent vertebrae. The anterior fixation blade includes an anterior alignment boss with two opposing outward extending anterior blades with end plate penetrating tips configured to fit within the open interior of the cage, the anterior alignment boss having first and second ends, the first end of the anterior alignment boss being rotatably coupled with a first opening in the annular side wall. The posterior fixation blade includes a posterior alignment boss with two opposing outward extending posterior blades with end plate penetrating tips configured to fit within the open interior of the cage, the posterior alignment boss having first and second ends, the first end being rotatably coupled to the second end of the anterior alignment boss and the second end of the posterior alignment boss being rotatably coupled with a second opening in the annular side wall opposite the first opening. The anterior and posterior fixation blades are counter-rotating blades and the anterior alignment boss and posterior alignment boss are configured to receive or engage a blade activation tool having an anterior engagement portion and a posterior engagement portion configured to rotate the anterior and posterior fixation blades from a stowed position to a deployed condition.

In many embodiments, the cage further includes a blade stop to prevent the blades from exceeding maximum deployment.

In many embodiments, the anterior and posterior blades further include a cutting edge between the boss and tip.

In many embodiments, the anterior and posterior blades are curved blades. The curved blades may be shaped to follow the annular side wall within the open interior.

In many embodiments, the anterior and posterior blades may be constructed of titanium, a titanium alloy, polyetherketoneketone (PEEK), or any other biologically acceptable materials, or a combination of the materials, capable of penetrating the end plate.

In many embodiments, the anterior engagement portion of the blade activation tool is configured to engage the first end of the anterior alignment boss and the posterior engagement portion is configured to engage the first end of the posterior alignment boss through an opening in the anterior alignment boss In many embodiments, when coupled, the anterior and posterior fixation blades are movable from a fixation blade insertion position for positioning the coupled anterior and posterior blades in the cage to a fixation blade retention position in which the coupled anterior and posterior fixation blades are moved apart and the first end of the anterior alignment boss is within the first opening in the annular side wall and the second end of the posterior alignment boss is within the second opening in the annular side wall. A C-clip may be used to keep the anterior and posterior fixation blades in the fixation blade retention position in the cage In many embodiments, the first and second openings in the annular side wall include grooves and the first end of the anterior boss and the second end of the posterior boss include bumps, the bumps configured to interact with the grooves and hold the anterior and posterior fixation blades in one or more positions.

In many embodiments, the upper and lower surface include outwardly projecting sharp raised ridges, teeth and/or striations.

In another aspect, embodiments of the present invention provide a stand-alone interbody fixation system having a cage with an annular side wall with an open interior and upper and lower surfaces having outwardly projecting sharp raised ridges, teeth and/or striations, the cage being configured to fit between end plates of adjacent vertebrae, an anterior fixation blade having an anterior alignment boss with two curved opposing outward extending anterior blades shaped to follow the annular side wall within the open interior, the blades being capable of penetrating the end plate, the anterior alignment boss being rotatably coupled to a first opening in the annular side wall, and a posterior fixation blade having a posterior alignment boss with two curved opposing outward extending posterior blades shaped to follow the annular side wall within the open interior, the blades being capable of penetrating the end plate, the posterior alignment boss being rotatably coupled to the anterior alignment boss and further rotatably coupled with a second opening in the annular side wall opposite the first opening. The anterior and posterior fixation blades are counter-rotating blades and are configured to receive or engage a counter-rotating blade activation tool configured to counter-rotate the anterior and posterior fixation blades from a stowed position to a deployed condition.

In many embodiments, the anterior and posterior blades further include end plate penetrating tips.

In many embodiments, the blade activation tool includes an anterior engagement portion configured to engage the anterior alignment boss and a posterior engagement portion configured to engage the posterior alignment boss.

In many embodiments, the first and second openings in the annular side wall include grooves and the anterior alignment boss and the posterior alignment boss include bumps, the bumps configured to interact with the grooves and hold the anterior and posterior fixation blades in one or more positions.

In many embodiments, the anterior and posterior blades may be constructed of titanium, a titanium alloy, polyetherketoneketone (PEEK), or any other biologically acceptable materials, or a combination of the materials, capable of penetrating the end plates. In another aspect, embodiments of the present invention provide a kit for a stand-alone interbody fixation system comprising a stand-alone interbody fixation system and a counter-rotating blade activation tool. The stand-alone interbody fixation system is configured to fit between end plates of adjacent vertebrae and attach to the end plates. The system comprising a cage having an annular side wall with open interior and upper and lower surfaces, an anterior fixation blade having an anterior alignment boss with two curved opposing outward extending anterior blades shaped to follow the annular side wall within the open interior, the blades being capable of penetrating the end plate, the anterior alignment boss being rotatably coupled to a first opening in the annular side wall, and a posterior fixation blade having a posterior alignment boss with two curved opposing outward extending posterior blades shaped to follow the annular side wall within the open interior, the blades being capable of penetrating the end plate, the posterior alignment boss being rotatably coupled to the anterior alignment boss and further rotatably coupled with a second opening in the annular side wall opposite the first opening. The counter-rotating blade activation tool being configured to counter-rotate the anterior and posterior fixation blades from a stowed position to a deployed condition.

In many embodiments, the kit further includes a bone graft or biologic material sized to fit within the interior of the cage when the anterior and posterior fixation blades are in the stowed position.

In many embodiments, the first and second openings in the annular side wall include grooves and the anterior alignment boss and the posterior alignment boss include bumps, the bumps configured to interact with the grooves and hold the anterior and posterior fixation blades in one or more positions.

In many embodiments, the anterior engagement portion of the blade activation tool is configured to engage a first end of the anterior alignment boss and the posterior engagement portion is configured to engage a first end of the posterior alignment boss through an opening in the anterior alignment boss.

BRIEF DESCRIPTION OF THE DRAWINGS

The present invention is described with reference to the accompanying drawings.

FIGS. 12A-16C show other embodiments of stand-alone interbody fixation systems.

DETAILED DESCRIPTION OF THE INVENTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Figure 1:
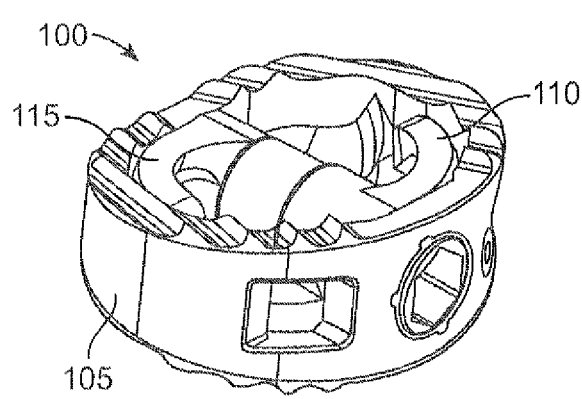
FIGS. 1-10K show various views of one embodiment of a stand-alone interbody fixation system.
Figure 2:
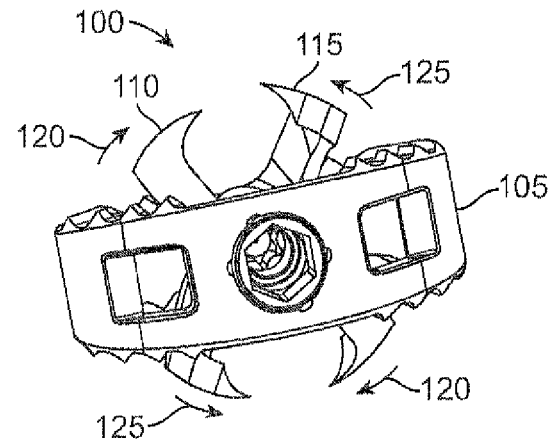

FIGS. 1 and 2 illustrate schematically one embodiment of a stand-alone interbody fixation system 100. The stand-alone interbody fixation system 100 is a pre-assembled multi-component design which integrates a fixation feature with an interbody spacer with no additional support required. In preferred embodiments, the system 100 is used in spinal fusion surgeries including, but not limited to Anterior Lumbar Interbody Fusion (ALIF), Posterior Lumbar Interbody Fusion (PLIF), or Transforaminal Lumbar Interbody Fusion (TLIF), lateral and cervical procedures, wherein two or more vertebrae are joined or fused together for the treatment of spinal disorders such as spondylolisthesis, scoliosis, severe disc degeneration, or spinal fractures. While the embodiments are described primarily in the context of an ALIF procedure, use with other procedures are also contemplated. The system 100 may be used in a variety of spinal procedures, including open procedures and minimally invasive surgery (MIS) procedures using low profile instrumentation which facilitates a less invasive approach through a smaller incision. As can be understood by one skilled in the art, these embodiments are shown for illustrative purposes and are not intended to limit the scope of the invention.

The unique design of the stand-alone interbody fixation system 100 provides a solid fixation in all aspects (flexion, extension, torsion, rotation, migration). In many embodiments, the system 100 is configured to use a single instrument to distract, insert and deploy the system. The design allows for multiple footprint shapes, ranging from 20-40 mm in both length and width to ensure adequate contact with cortical rim. In many embodiments, the design includes a tapered leading portion that allows smooth insertion and deployment. The height may range from 8-20 mm, but other heights are also contemplated, depending on location. Lordosis ranging from 0-20 degrees to accommodate surgical needs.

The system 100 disclosed uses counter rotating blades 110, 115 that provide 4 points of fixation with 2-10 mm of blade engagement. In order to maintain bone purchase or blade engagement for each implant height and footprint, the blade length may be increased or decreased to accommodate the cage height. As the blade rotates from its resting position to the deployed position, the amount of exposed blade is controlled across the various implant sizes. While counter rotating blades are disclosed, other embodiments may deploy the blades rotating in the same direction. Secure deployment and engagement of blades with positive feedback when blades deployed and locked. Internal lock prevents accidental deployment and positive tangible feedback to surgeon when the blades are fully deployed. The blades are securely held in place and some embodiments may include elements to prevent over-deployment. In some embodiments, the ability to reverse deployment and remove or reposition implant may be desirable. The unique blade shape allows adequate space to pack bone graft before insertion. There are also access ports in the interbody spacer or cage to allow additional bone graft to be added after insertion/deployment. Some embodiments of the blade shape geometry may also pull the endplates together when deployed.

Figure 3:
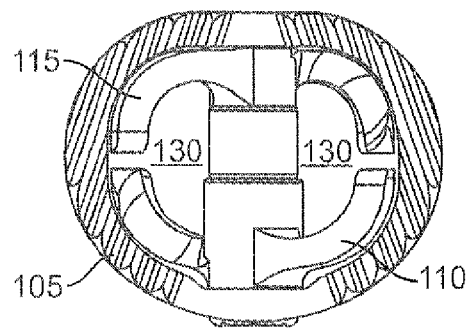
Figure 4:
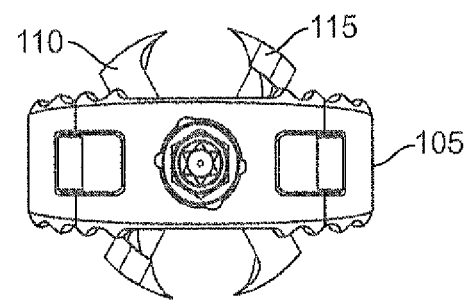
Figure 5A:
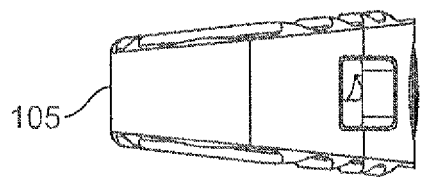
Figure 5B:
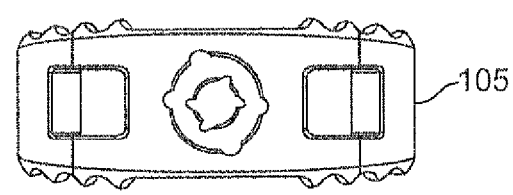

The stand-alone interbody fixation system 100 includes a cage 105, an anterior fixation blade 110 and a posterior fixation blade 115. FIG. 1 is a perspective view showing the anterior 110 and posterior 115 blades within the cage 105 in a delivery position and FIG. 2 is a perspective view showing the anterior 110 and posterior 115 blades in the deployed position. FIG. 3 is a top view showing an embodiment in which the curved anterior 110 and posterior 115 blades are designed to follow shape of the interior of the cage 105 resulting in axial windows 130 that may be used for packing of bone graft material within to expedite the fusion of the cage in the spinal column. FIG. 4 is a view looking posteriorly showing the cage 105 and the anterior 110 and posterior 115 blades in the deployed position. FIG. 5A is a side view and FIG. 5B is a front view of the cage 105 and the anterior 110 and posterior 115 blades in the stowed position.

In an ALIF procedure, the stand-alone interbody fixation system 100 is inserted and fixated from an anterior approach so that posterior muscular structures are preserved and surgical morbidity associated with 360° is eliminated. Once inserted, the anterior fixation blade 110 rotates in a clockwise rotation 120 and the posterior fixation blade 115 rotates in a counterclockwise rotation 125, shown in FIG. 2, biting into the vertebral end plates (not shown). While embodiments below are described primarily in the context of two counter rotating blades, other number of blades and rotations are also contemplated.

Figure 6A:
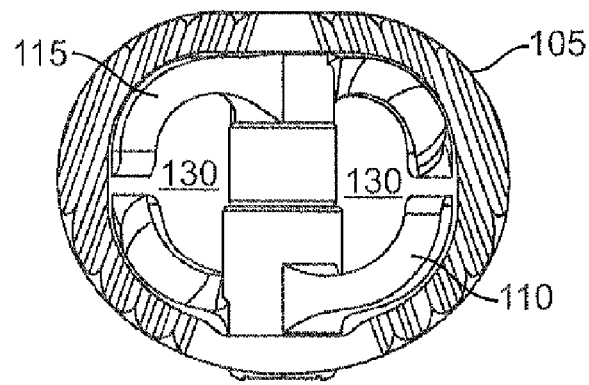
Figure 6B:
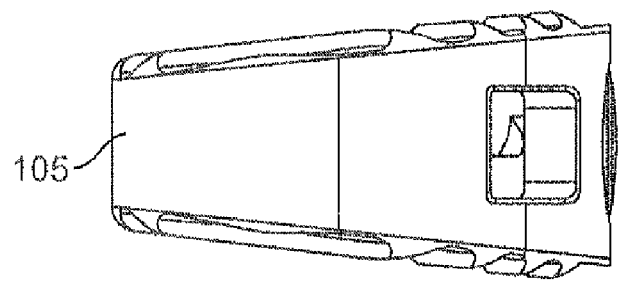
Figure 6C:
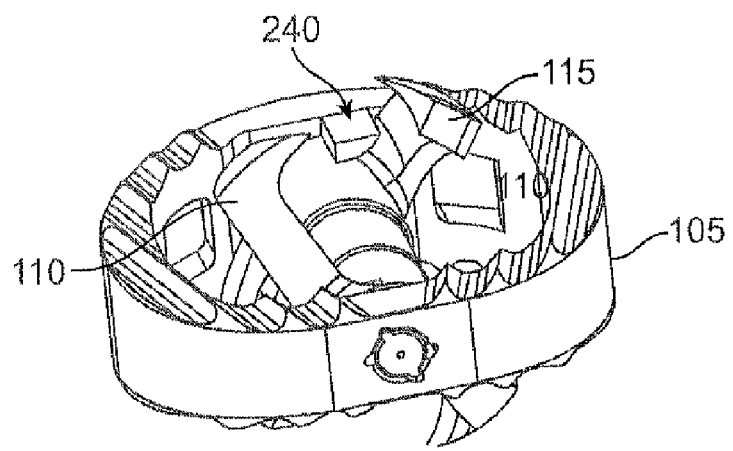

FIGS. 6A-6C show some of the assembly features of the stand-alone interbody fixation system 100. FIG. 6A is a top view showing the anterior 110 and posterior 115 blades positioned for insertion with the axial window 130 between for placement of bone graft or other types of bone growth materials or biologics (not shown). FIG. 6B is a side view showing that when the anterior 110 and posterior 115 blades in the stowed or rest position they are under the boundaries or surfaces of the cage 105 geometry. This allows the system 100 to be inserted between the end plates of adjacent vertebrae without anterior 110 and posterior 115 blades contacting the end plates. FIG. 6C is a perspective view of the system showing a stop 240 on the cage 105 that the anterior 110 and posterior 115 blades may contact during deployment to prevent the blades from exceeding maximum deployment.

Figure 7A:
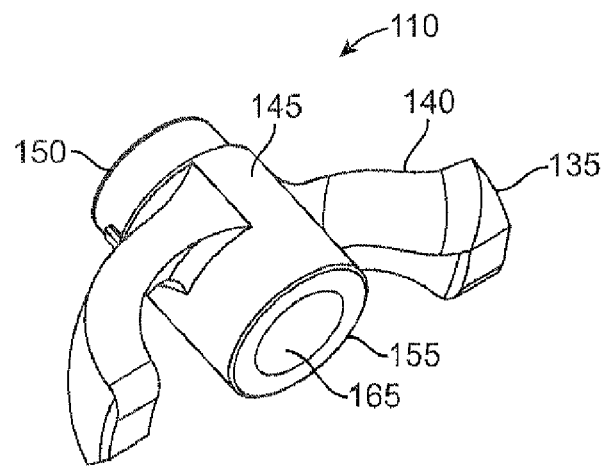
Figure 7B:
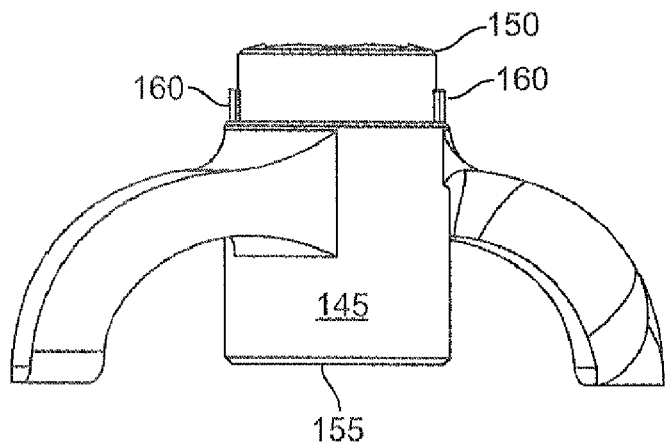
Figure 7C:
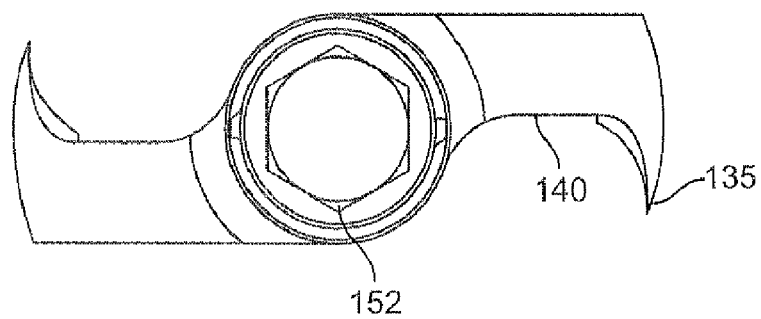
Figure 8A:
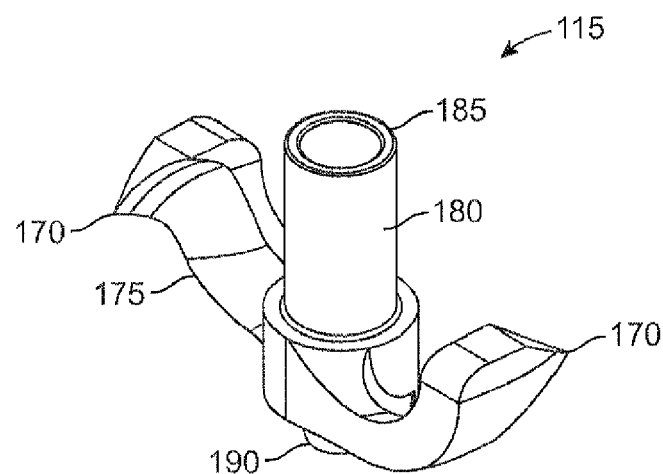
Figure 8B:
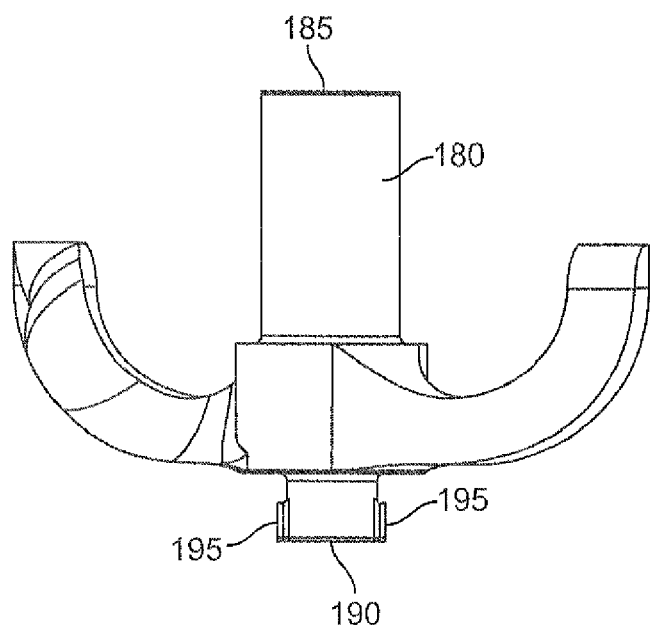
Figure 8C:
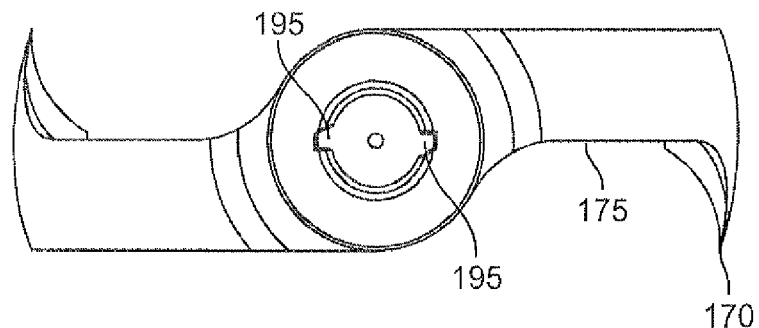
Figure 8D:
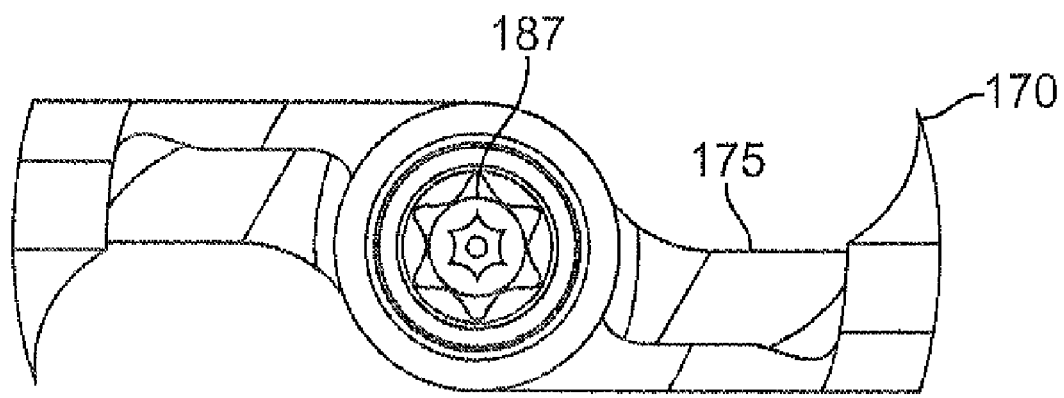
Figure 8E:
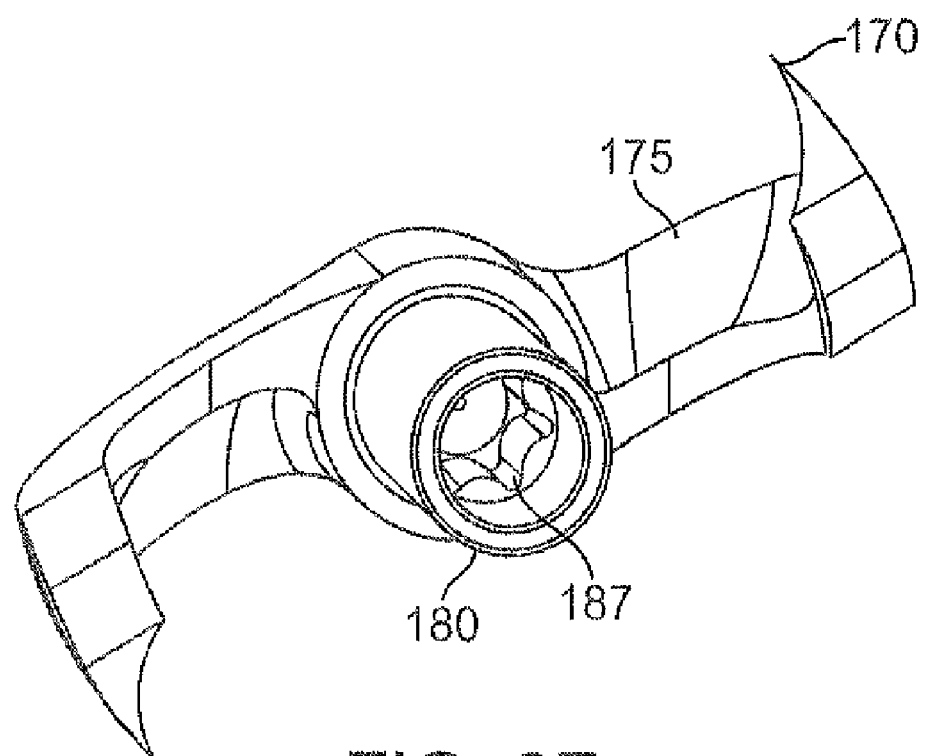
Figure 9A:
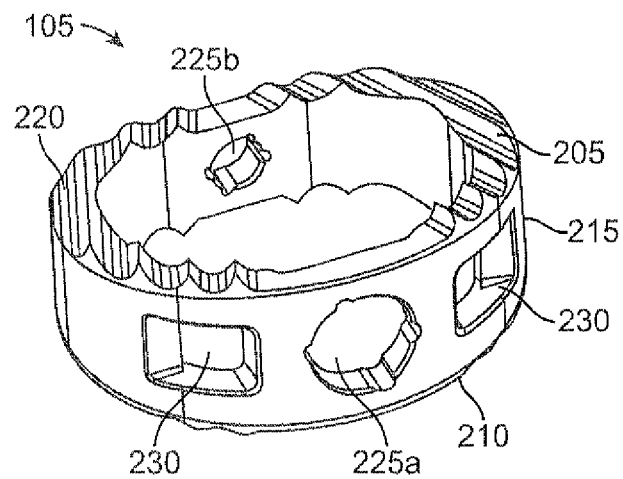
Figure 9B:
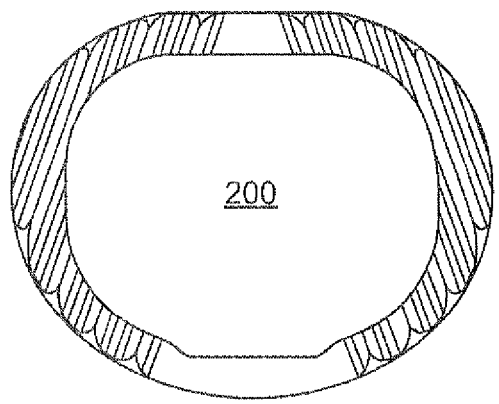
Figure 9C:
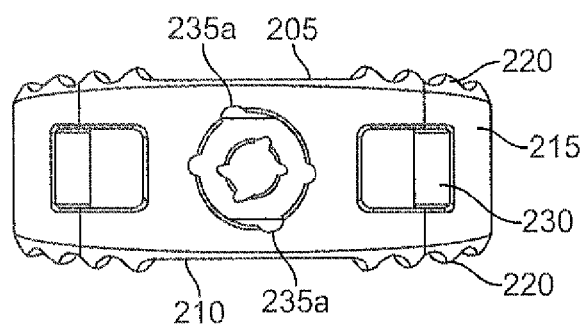
Figure 9D:
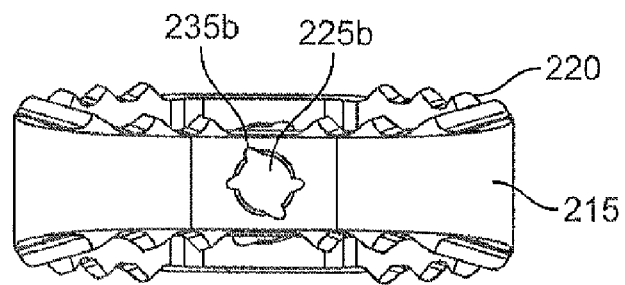
Figure 9E:
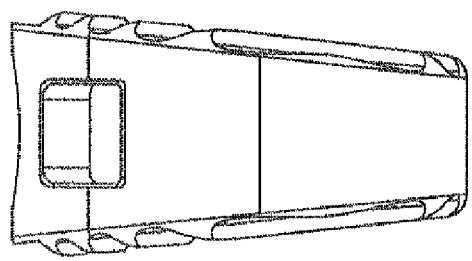
Figure 9F:
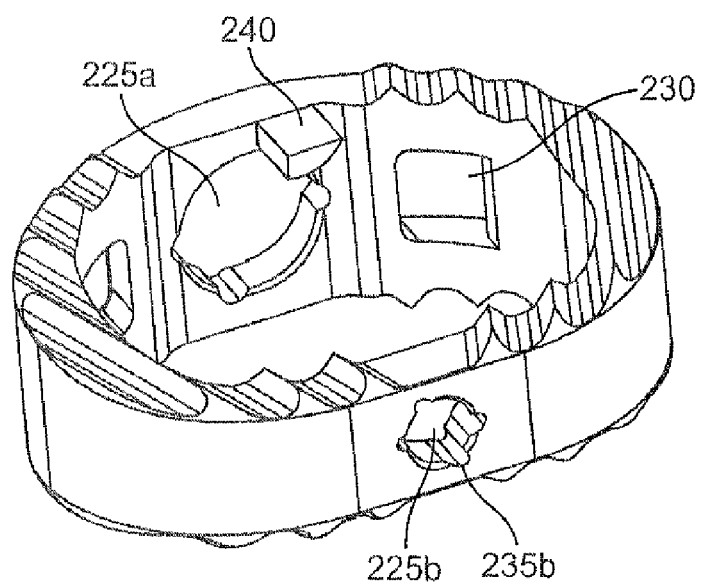

FIGS. 7A-7C show one embodiment of an anterior fixation blade 110 that includes curved blades designed to penetrate the end plates of adjacent vertebrae. The curved blades may have a smooth curve or may be a series of straight sections. Using curved blades maximizes graft volume and minimizes graft displacement during deployment. The anterior fixation blade 110 may be constructed of titanium, a titanium alloy, polyetherketoneketone (PEEK), or any other biologically acceptable materials that would engage the spine plate and provide a rigid structure. The anterior fixation blade 110 may be constructed using one material or a combination of the materials. The anterior fixation blade 110 includes blade tips 135 that are designed to penetrate bone with a sharp tip feature and continue to a leading edge or cutting edge 140, similar to a sickle. The blade tips 135 positioned at the outer perimeter of an anterior fixation blade 110 diameter facilitate immediate bone engagement at initial deployment. The blades are attached to an axial alignment boss 145. The blades include cutting edge that spans the entire length of the blade from the boss to the tip for all sizes. The axial alignment boss 145 has a first end 150 and a second end 155. The first end 150 includes a cylindrical rotating alignment feature that includes one or more blade resistance/securing/locking feature 160 that couples to the cage 105 (discussed below). The first end 150 further includes a drive mechanism 152 or recess configured to engage a deployment instrument for rotating the anterior fixation blade 110 between a closed and open position. The drive mechanism may be a Hex, Hex-a-lobe, spline, double hex, Bristol, polydrive, torq-set, square, slotted, Phillips, etc. The second end 155 of the boss 145 includes an opening 165 configured to interact with the posterior fixation blade 115 and also allows insertion of the deployment instrument for actuation of the posterior fixation blade 115.

FIGS. 8A-8E show one embodiment of a posterior fixation blade 115 that includes curved blades designed to penetrate the end plates of adjacent vertebrae. Smooth curved or a series of straight sections that form the curved blades maximize graft volume and minimize graft displacement during deployment. The posterior fixation blade 115 may be constructed of titanium, a titanium alloy, polyetherketoneketone (PEEK), or any other biologically acceptable inert materials that would provide a rigid structure. The posterior fixation blade 115 may also be constructed with a combination of the materials. The posterior fixation blade 115 includes blade tips 170 that are designed to penetrate with a sharp tip feature and continue to a sharp leading edge or cutting edge 175, similar to a sickle. The blade tips 170 at the outer perimeter of the diameter facilitate immediate bone engagement at initial deployment.

The blades are attached to an axial alignment boss 180. The blades include cutting edge that spans the entire length of the blade from the boss to the tip for all sizes. The axial alignment boss 180 has a first end 185 and a second end 190. The first end 185 is designed to slidably fit within the opening 165 of the anterior fixation blade 110. The first end 185 further includes a drive mechanism 187 or recess for rotating the blade between a closed and open position. The drive mechanism may be a Hex, Hex-a-lobe, spline, double hex, Bristol, polydrive, torq-set, square, slotted, Phillips, etc. The second end 190 includes a cylindrical rotating alignment feature that includes one or more blade resistance/securing/locking feature 195 configured to couple with the cage 105.

FIGS. 9A-9F show different views and features of the cage 105. The cage 105 may be made of a rigid construction and preferably provided in several different sizes and shapes to fill differently sized evacuated spaces in differently sized individuals. The cage 105 has an interior opening 200 for storage of the blades 110, 115. The curves shape of the blades 110, 115 allow packing of bone graft material (see FIG. 3). The cage 105 may be constructed of a radiolucent material, such as polyetherketoneketone (PEEK), a commercially pure titanium, a titanium alloy or any other biologically acceptable inert materials that would provide the cage with a rigid structure.

The cage 105 is annular in configuration having an upper surface 205 and an opposed lower surface 210 configured to engage superiorly and inferiorly the end plates of adjacent vertebrae, and an annular side wall 215 around the hollow interior opening 200. The annular side wall 215 may have varying height, length, and thickness, and may include lordotic angle for better anatomical fit. In some embodiments, a plurality of outwardly projecting sharp raised ridges/teeth/striations 220 are formed on the surfaces 205, 210 for biting into and gripping the vertebral end plates (not shown). The ridges 220 may have a variable thickness, height, and width as well as an angle with respect to surfaces. The ridges 220 may be disposed at slightly offset angles with respect to each other or, alternatively with respect to the ridges on different portions of the cage, to reduce the possibility of the ridges sliding in any direction along the end plates and to prevent rotation of the cage on the end plate. For example, the figures show the ridges 220 on one side or portion of the surface 205 are all in parallel alignment, but misaligned with the ridges on the other side or portion. While it may be preferable that the ridges 220 are identical in configuration on the upper and lower surfaces, in some embodiments, the ridges or teeth different or have a different pattern for each surface.

A plurality of openings 225, 230 are disposed in the side wall 215 of the cage 105. Opening 225*a* is configured to receive or engage end 150 of fixation blade 110 and opening 225*b* is configured to receive or engage end 190 of fixation blade 115. Other openings 230 spaced about the cage may be configured to receive or engage an insertion tool or blade activation tool (not shown), or used to pack bone or other suitable bone graft material. Openings 225*a*, 225*b* are generally circular in shape and include blade resistance/locking features 235*a*, 235*b* to hold blades in one or more positions. These features 235*a*, 235*b* may include grooves, notches or dimples that couple or interact with ridges, tabs or bumps 160, 195 on blades 110, 115. When end 150 of fixation blade 110 is inserted into opening 225*a*, bumps 160 interact with one of the grooves 235*a*. As the blade is rotated, the bumps 160 may move from one set of grooves 235*a* in a stored position to another set of grooves 235*a* in the deployed position, to form a locking mechanism. When end 190 of fixation blade 115 is inserted into opening 225*b*, bumps 195 interact with one of the grooves 235*b*. As the blade is rotated, the bumps 195 may move from one set of grooves 235*b* in a stored position to another set of grooves 235*a* in the deployed position, to form a locking mechanism. Openings 230 may be generally rectangular in shape to accommodate an insertion tool or blade activation tool having a center blade activation portion disposed between a pair of prongs, so that the tool can grip the openings 230 of the cage and/or rotate the blades. A blade stopping feature 240 may also be used to contact the blades and prevent the blades from rotating more then desired angle.

Figure 10A:
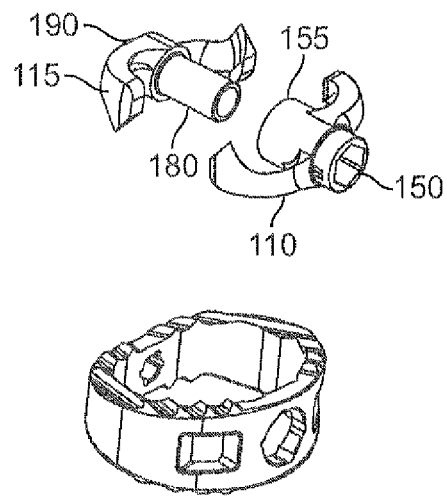
Figure 10B:
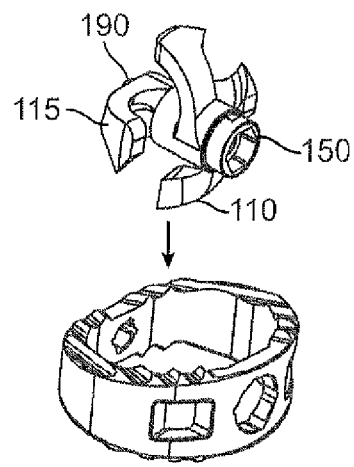
Figure 10C:
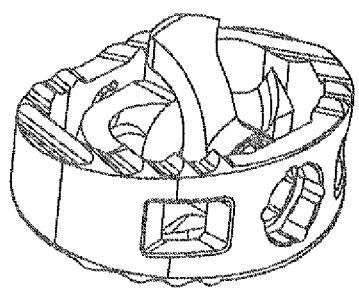
Figure 10D:
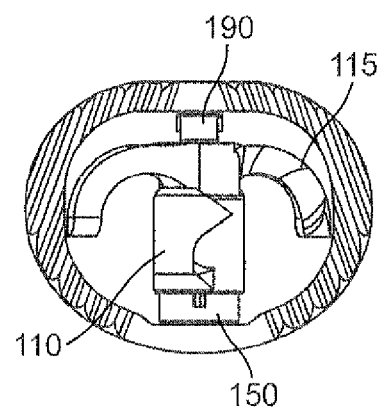
Figure 10E:
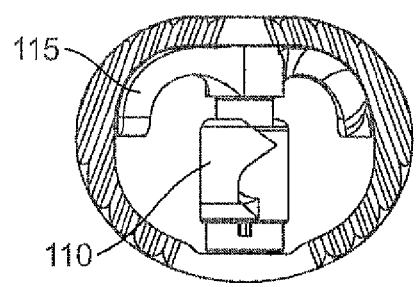
Figure 10F:
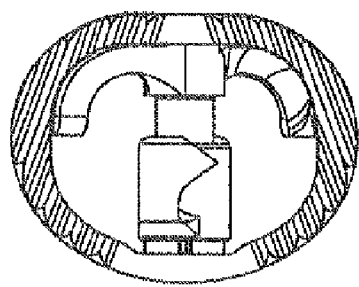
Figure 10G:
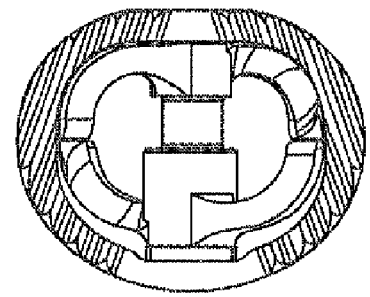
Figure 10H:
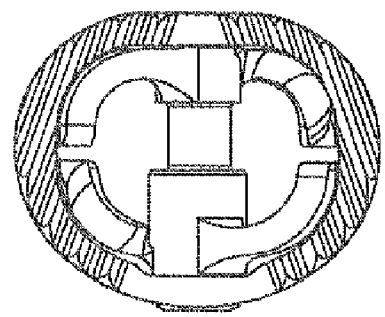
Figure 10I:
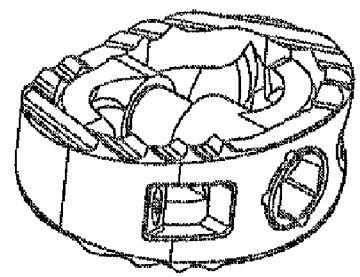
Figure 10J:
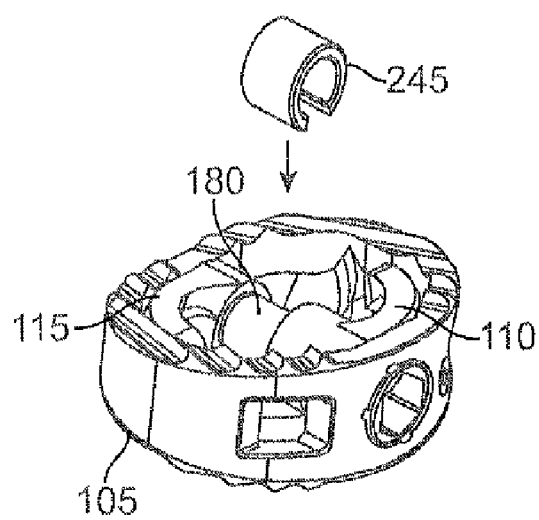
Figure 10K:
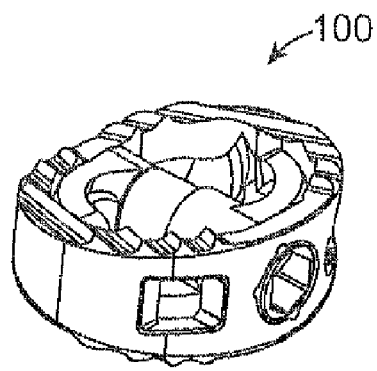

FIGS. 10A-10H show one example of an assembly method for system 100. The anterior fixation blade 110 and posterior fixation blade 115 are aligned (FIG. 10A) and the first end 185 of the posterior fixation blade 115 is inserted into the opening 160 near the second end 155 of the anterior fixation blade 110. When fully inserted, the distance between the first end 150 of the anterior fixation blade 110 and the second end 190 of the posterior fixation blade 115 is less than an interior distance between the first opening 225*a* and second opening 225*b* of the cage 105 (FIG. 10B). With the blades 110, 115 combined in this manner, they may be inserted into the central opening 200 and positioned within the cage 105 (FIGS. 10C, 10D). The blades 110, 115 may then be moved or extended in opposite directions until the first end 150 of the anterior fixation blade 110 is inserted into the first opening 225*a* and the second end 190 of the posterior fixation blade 115 is inserted into the second opening 225*b* and the blades are rotated to the stored position (FIGS. 10E-10I). To keep the blades 110, 115 in the extended position, a C-clip 245 is slid over the boss 180 of the posterior fixation blade 115 (FIG. 10J) to keep the ends of the anterior and posterior fixation blades 110, 115 within the openings 225*a*, 225*b* forming the system 100 (FIG. 10K).

Figure 11:
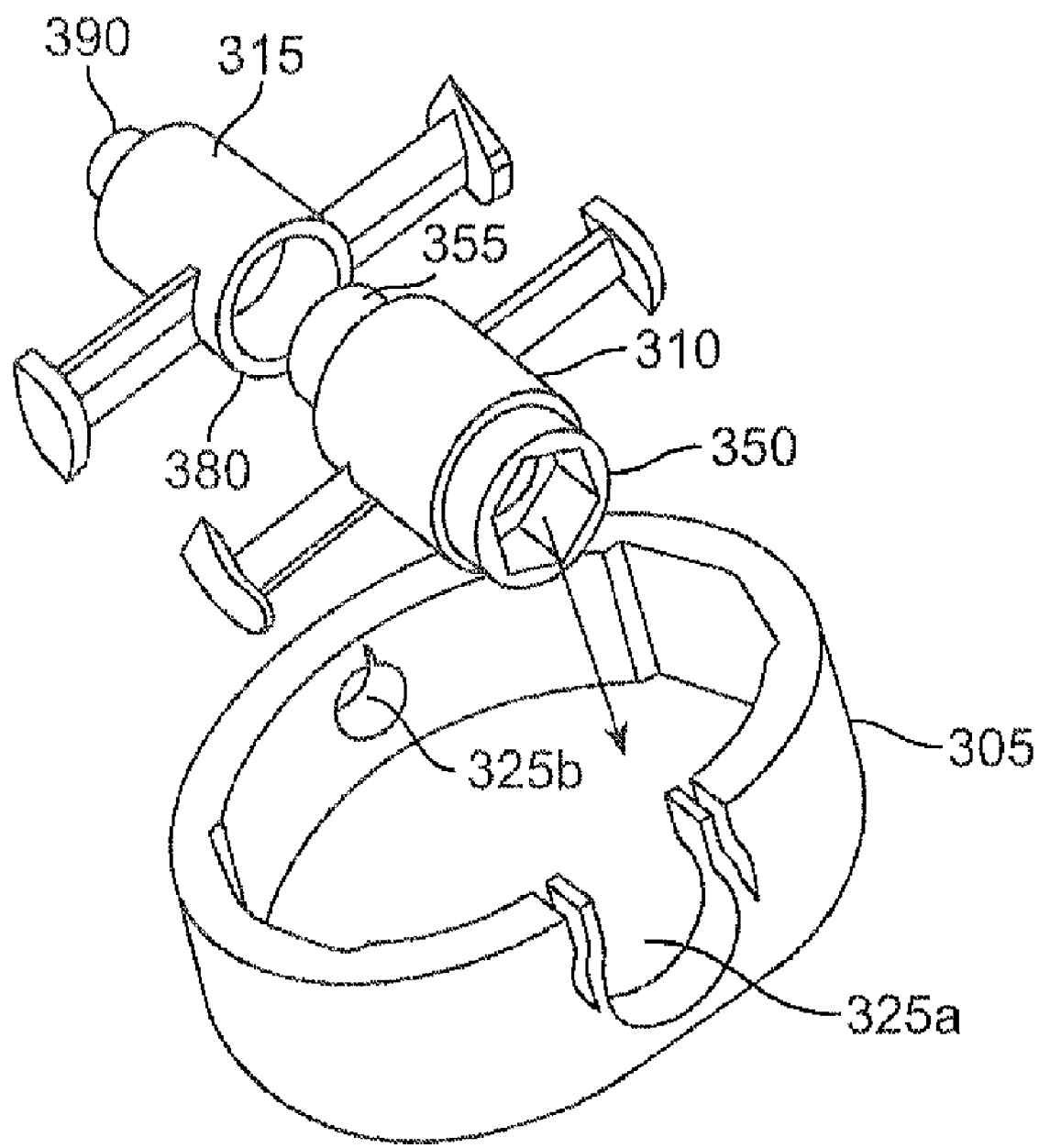
FIG. 11 shows another assembly embodiment of a stand-alone interbody fixation system.
Figure 17A:
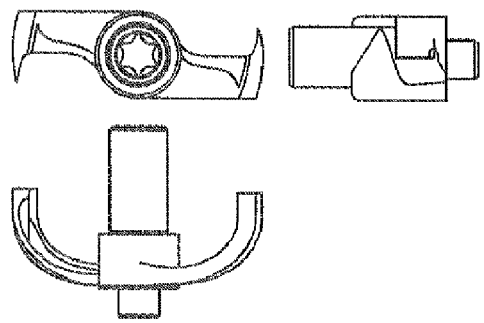
FIG. 17 shows other embodiments of anterior and/or posterior blades.
Figure 17B:
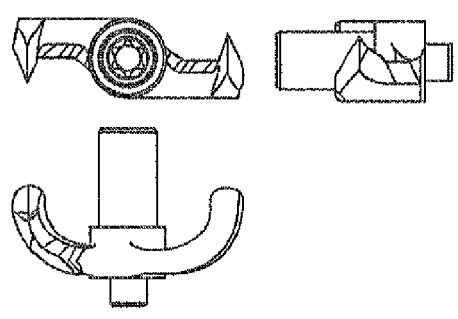
Figure 17C:
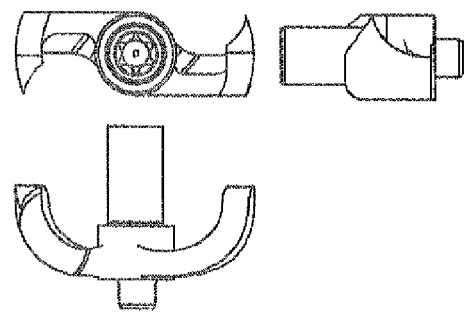
Figure 17D:
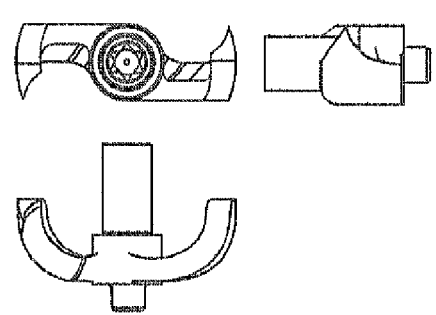

FIG. 11 is an exploded view showing another embodiment of a stand-alone interbody fixation system 300, having a cage 305, an anterior fixation blade 310 and a posterior fixation blade 315. The cage 305 may be similar to cage 105 and may include one or more of the features disclosed above for cage 105. The anterior and posterior fixation blades 310, 315 may include one or more of the features disclosed above for blades 110, 115. In the embodiment shown, the anterior and posterior fixation blades 310, 315 are straight. The cage 305 includes a first opening 325*a* with an open top portion configured to couple with a first end 350 of the anterior fixation blade 310 and a second opening 325*b* configured to couple with a second end 390 of the posterior blade 315. To assemble the system 300, a first end 380 of the posterior fixation blade 315 is coupled with a second end 355 of the anterior fixation blade 310. The joined fixation blades 310, 315 are then advanced toward the cage 305 and the second end 390 of the posterior fixation blade 315 is inserted into the second opening 325*b*. The first end 350 of the anterior fixation blade 310 is inserted into the open top portion of the first opening 325*a*, snapping in place. The first opening 325*a* may have spring like side portions that hold the first end 350 of the anterior fixation blade 310 in place. The ends 350, 390 of the blades may also include ridges, tabs or bumps that engage or couple with grooves, notches or dimples in openings 325*a* and 325*b*, similar to those disclosed above for system 100.

FIGS. 12A-16C show different embodiments of stand-alone interbody fixation systems which integrates a fixation feature with an interbody spacer with no additional support required. One or more of the elements and feature disclosed above for the stand-alone interbody fixation system 100 and 300 may be incorporated into the systems below.

FIGS. 12A and 12B show one embodiment of a stand-alone single anterior blade interbody fixation system 400 having one fixation blade 410, with multiple axial graft windows 430 and transverse inner walls. In this embodiment, the fixation blade 410 is a true s-shaped blade positioned toward a front portion of the implant and may used for anterior fixation (a reversed design with the blade toward the back portion may be for posterior fixation) and the transverse inner walls create a robust cage with center struts and allow axial graft windows.

FIGS. 13A and 13B show another embodiment of a stand-alone double blade interbody fixation system 500 having two fixation blades 510, 515, central graft window 530 and transverse inner walls. This embodiment includes fixation blades that are true s-shaped blades positioned on opposite sides of the central graft window 530 for anterior and posterior fixation, and the transverse inner walls create a robust cage with center struts and allow a larger axial graft window.

FIGS. 14A and 14B show another embodiment of a stand-alone single anterior blade interbody fixation system 600 having a single blade 610 with multiple cutting edges, posterior graft window and transverse inner wall. The multiple cutting edges of the fixation blade are true s-shaped with sharp tips used for anterior to posterior fixation, including midline fixation. The transverse inner wall create a robust cage and allows posterior graft window.

FIGS. 15A-15C show another embodiment of a stand-alone interbody fixation system 700 having two fixation blades 710, 715, with multiple cutting edges and graft window. This embodiment includes fixation blades that are true s-shaped blades for fixation, and superior anterior and posterior fixation.

FIGS. 16A-16C show another embodiment of a stand-alone interbody fixation system 800 two fixation blades 810, 815 with multiple cutting edges and graft window. This embodiment includes fixation blades with the maximum achievable blade length and simple blade to cage assembly.

FIGS. 17A-17D are views showing other embodiments of anterior and/or posterior blades suitable for use in the embodiments disclosed above. The blades may be curved blades having a smooth curve or may be a series of straight sections or both. The blades may also vary in thickness in both height and width.

Instrument Concepts/Features

Figure 18A:
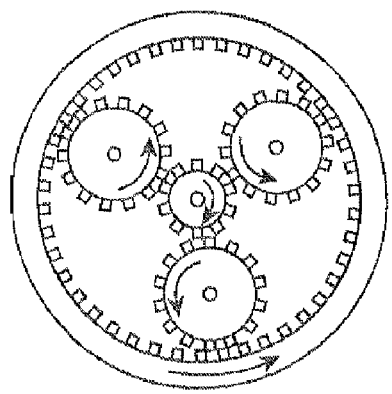
FIGS. 18A-20 show embodiments of deployment instrument for use with stand-alone interbody fixation systems.
Figure 18B:
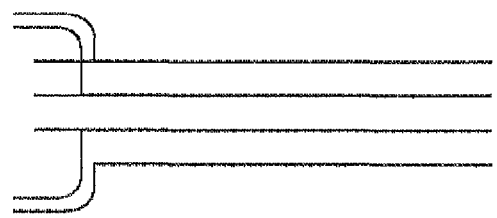
Figure 18C:
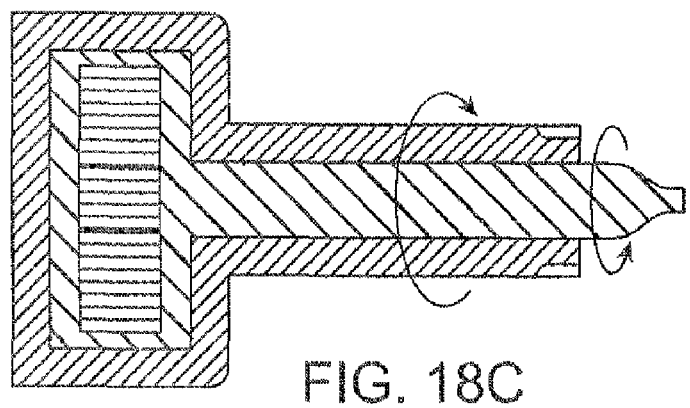
Figure 19A:
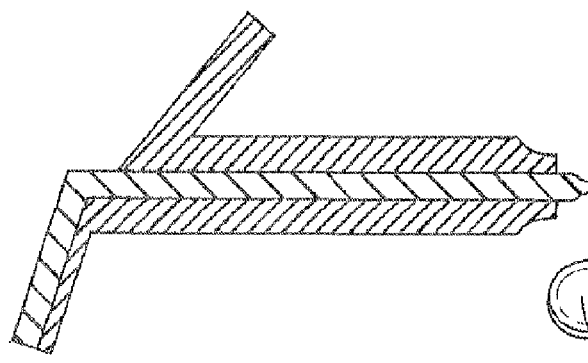
Figure 19B:
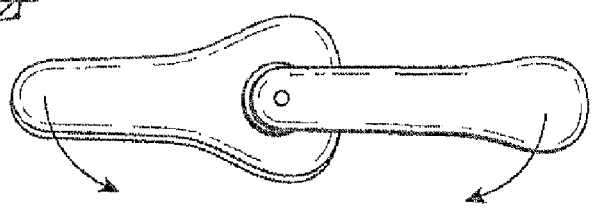

In some embodiments the deployment instrument will have two concentric counter rotating shafts. The counter-rotation can be achieved with a series gears (shown in FIGS. 18A-18C) or with two levers (shown in FIGS. 19A-19B). The tip of the instrument may have an interference fit to fixate to the implant. The implant holder will be cannulated to allow the blade deployment instrument to pass through. The implant inserter/distractor will also be cannulated to allow the deployment shafts to pass through.

Figure 20A:
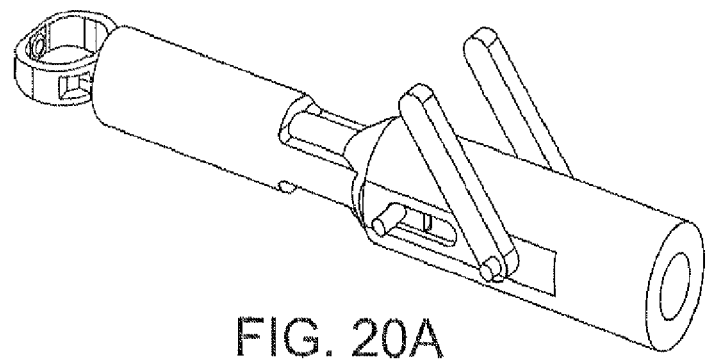
Figure 20B:
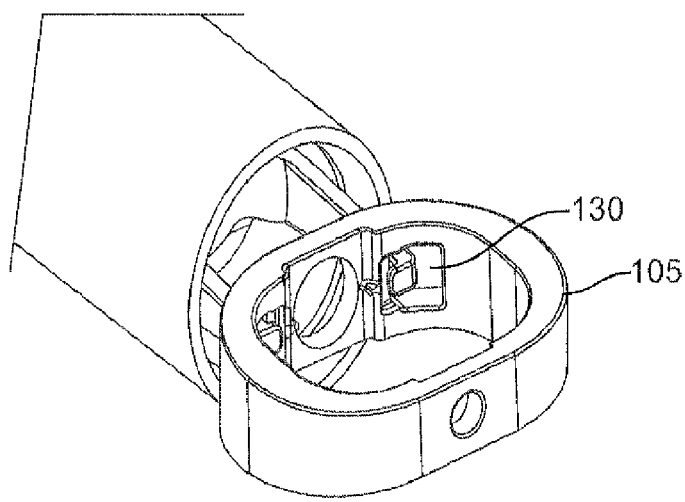
Figure 20C:
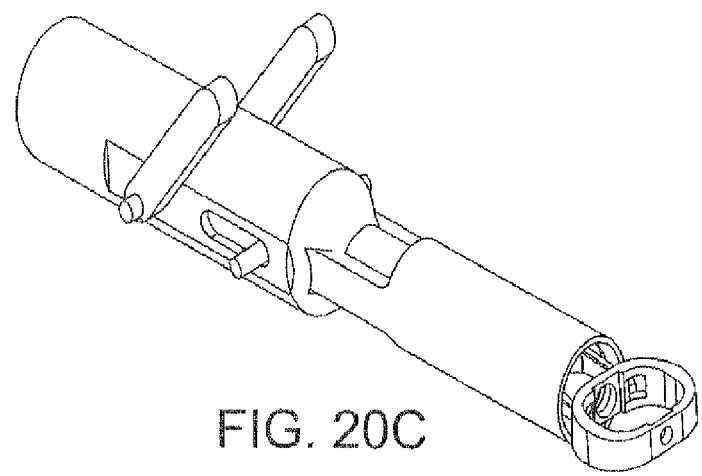

FIGS. 20A-20C show another embodiment of a deployment instrument interacting with the cage 105. Handles are used to deploy the blades (not shown).

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A stand-alone interbody fixation system comprising:
a cage having an annular side wall with an open interior and upper and lower surfaces, the cage being configured to fit between end plates of adjacent vertebrae;
an anterior fixation blade having an anterior alignment boss with two opposing outward extending anterior blades with end plate penetrating tips configured to fit within the open interior of the cage, the anterior alignment boss having first and second ends, the first end of the anterior alignment boss being rotatably coupled with a first opening in the annular side wall; and
a posterior fixation blade having a posterior alignment boss with two opposing outward extending posterior blades with end plate penetrating tips configured to fit within the open interior of the cage, the posterior alignment boss having first and second ends, the first end being rotatably coupled to the second end of the anterior alignment boss and the second end of the posterior alignment boss being rotatably coupled with a second opening in the annular side wall opposite the first opening;
wherein when coupled, the anterior and posterior fixation blades are movable from a fixation blade insertion position for positioning the coupled anterior and posterior blades in the cage to a fixation blade retention position in which the coupled anterior and posterior fixation blades are moved apart and the first end of the anterior alignment boss is within the first opening in the annular side wall and the second end of the posterior alignment boss is within the second opening in the annular side wall; and
a C-clip positioned between the anterior and posterior fixation blades configured to keep the anterior and posterior fixation blades in the fixation blade retention position in the cage;
wherein the anterior and posterior fixation blades are counter-rotating blades and the anterior alignment boss and posterior alignment boss are configured to receive or engage a deployment instrument having an anterior engagement portion and a posterior engagement portion configured to rotate the anterior and posterior fixation blades from a stowed position to a deployed condition.

2. The system of claim 1, wherein the cage further includes a blade stop to prevent the blades from exceeding maximum deployment.

3. The system of claim 1, wherein the anterior and posterior blades further include a cutting edge between the boss and tip.

4. The system of claim 1, wherein the anterior and posterior blades are curved blades.

5. The system of claim 4, wherein the curved blades are shaped to follow the annular side wall within the open interior.

6. The system of claim 1, wherein the anterior and posterior blades may be constructed of titanium, a titanium alloy, polyetherketoneketone (PEEK), or any other biologically acceptable materials, or a combination of the materials, capable of penetrating the end plate.

7. The system of claim 1, wherein the anterior engagement portion of the deployment instrument is configured to engage the first end of the anterior alignment boss and the posterior engagement portion is configured to engage the first end of the posterior alignment boss through an opening in the anterior alignment boss.

8. The system of claim 1, wherein the first and second openings in the annular side wall include grooves and the first end of the anterior boss and the second end of the posterior boss include bumps, the bumps configured to interact with the grooves and hold the anterior and posterior fixation blades in one or more positions.

9. The system of claim 1, wherein the upper and lower surface include outwardly projecting sharp raised ridges, teeth and/or striations.

10. A stand-alone interbody fixation system comprising:
a cage having an annular side wall with an open interior and upper and lower surfaces having outwardly projecting sharp raised ridges, teeth and/or striations, the cage being configured to fit between end plates of adjacent vertebrae;
an anterior fixation blade having an anterior alignment boss with two curved opposing outward extending anterior blades shaped to follow the annular side wall within the open interior, the blades being capable of penetrating the end plate, the anterior alignment boss being rotatably coupled to a first opening in the annular side wall; and
a posterior fixation blade having a posterior alignment boss with two curved opposing outward extending posterior blades shaped to follow the annular side wall within the open interior, the blades being capable of penetrating the end plate, the posterior alignment boss being rotatably coupled to the anterior alignment boss and further rotatably coupled with a second opening in the annular side wall opposite the first opening;
wherein when coupled, the anterior and posterior fixation blades are movable from a fixation blade insertion position for positioning the coupled anterior and posterior blades in the cage to a fixation blade retention position in which the coupled anterior and posterior fixation blades are moved apart and the first end of the anterior alignment boss is within the first opening in the annular side wall and the second end of the posterior alignment boss is within the second opening in the annular side wall; and
a C-clip positioned between the anterior and posterior fixation blades configured to keep the anterior and posterior fixation blades in the fixation blade retention position in the cage;
wherein the anterior and posterior fixation blades are counter-rotating blades and are configured to receive or engage a counter-rotating deployment instrument configured to counter-rotate the anterior and posterior fixation blades from a stowed position to a deployed condition.

11. The system of claim 10, wherein the anterior and posterior blades further include end plate penetrating tips.

12. The system of claim 10, wherein the deployment instrument includes an anterior engagement portion configured to engage the anterior alignment boss and a posterior engagement portion configured to engage the posterior alignment boss.

13. The system of claim 10, wherein the first and second openings in the annular side wall include grooves and the anterior alignment boss and the posterior alignment boss include bumps, the bumps configured to interact with the grooves and hold the anterior and posterior fixation blades in one or more positions.

14. The system of claim 10, wherein the anterior and posterior blades may be constructed of titanium, a titanium alloy, polyetherketoneketone (PEEK), or any other biologically acceptable materials, or a combination of the materials, capable of penetrating the end plates.

15. A kit for a stand-alone interbody fixation system comprising:
a stand-alone interbody fixation system configured to fit between end plates of adjacent vertebrae and attach to the end plates comprising:
a cage having an annular side wall with open interior and upper and lower surfaces;
an anterior fixation blade having an anterior alignment boss with two curved opposing outward extending anterior blades shaped to follow the annular side wall within the open interior, the blades being capable of penetrating the end plate, the anterior alignment boss being rotatably coupled to a first opening in the annular side wall;
a posterior fixation blade having a posterior alignment boss with two curved opposing outward extending posterior blades shaped to follow the annular side wall within the open interior, the blades being capable of penetrating the end plate, the posterior alignment boss being rotatably coupled to the anterior alignment boss and further rotatably coupled with a second opening in the annular side wall opposite the first opening,
wherein when coupled, the anterior and posterior fixation blades are movable from a fixation blade insertion position for positioning the coupled anterior and posterior blades in the cage to a fixation blade retention position in which the coupled anterior and posterior fixation blades are moved apart and the first end of the anterior alignment boss is within the first opening in the annular side wall and the second end of the posterior alignment boss is within the second opening in the annular side wall; and
a C-clip positioned between the anterior and posterior fixation blades configured to keep the anterior and posterior fixation blades in the fixation blade retention position in the cage; and
a counter-rotating deployment instrument configured to counter-rotate the anterior and posterior fixation blades from a stowed position to a deployed condition.

16. The kit of claim 15, further comprising a bone graft or biologic material sized to fit within the interior of the cage when the anterior and posterior fixation blades are in the stowed position.

17. The system of claim 15, wherein the first and second openings in the annular side wall include grooves and the anterior alignment boss and the posterior alignment boss include bumps, the bumps configured to interact with the grooves and hold the anterior and posterior fixation blades in one or more positions.

18. The kit of claim 15, wherein the anterior engagement portion of the deployment instrument is configured to engage a first end of the anterior alignment boss and the posterior engagement portion is configured to engage a first end of the posterior alignment boss through an opening in the anterior alignment boss.

* * * * *